United States Patent
Harte et al.

(10) Patent No.: US 9,285,350 B2
(45) Date of Patent: Mar. 15, 2016

(54) SOAK CHAMBER AND SYSTEM TO MEASURE THE SEED DENSITY HYDRATION PROFILE OF SEEDS

(71) Applicant: University of Tennessee Research Foundation, Knoxville, TN (US)

(72) Inventors: Federico Harte, Knoxville, TN (US);
Vinay Mannam, Knoxville, TN (US);
Stacy Worley, Coffeyville, KS (US);
John Wilkerson, Knoxville, TN (US);
David Smith, Knoxville, TN (US)

(73) Assignee: Bush Brothers & Co., Knoxville, TN (US)

( * ) Notice: Subject to any disclaimer, the term of this patent is extended or adjusted under 35 U.S.C. 154(b) by 424 days.

(21) Appl. No.: 13/871,347

(22) Filed: Apr. 26, 2013

(65) Prior Publication Data

US 2014/0318240 A1    Oct. 30, 2014

(51) Int. Cl.
*G01N 9/36* (2006.01)
*G01N 33/02* (2006.01)
*G01N 5/02* (2006.01)

(52) U.S. Cl.
CPC . *G01N 33/02* (2013.01); *G01N 5/02* (2013.01)

(58) Field of Classification Search
None
See application file for complete search history.

(56) References Cited

U.S. PATENT DOCUMENTS

| | | | | |
|---|---|---|---|---|
| 6,453,609 | B1 * | 9/2002 | Soll et al. | 47/57.6 |
| 7,547,852 | B2 * | 6/2009 | Sallovitz | 177/50 |
| 2006/0248943 | A1 * | 11/2006 | Funk | 73/32 R |

OTHER PUBLICATIONS

Xu, Shan, "Development and application of an automatic system for determing seed volume kinetics during soaking." Master's Thesis, Univeristy of Tennessee, 2010.

* cited by examiner

*Primary Examiner* — Robert R Raevis
(74) *Attorney, Agent, or Firm* — Pitts & Lake, P.C.

(57) ABSTRACT

Apparatuses, systems, and methods for measuring the hydration profile of seeds during Soaking. In some example embodiments, the volume change of irregular-shaped seeds during soaking is measured as the difference in the volume for a given chamber and the volume of water to fill a chamber with seeds at pre-defined time intervals. A device according to some example embodiments of the present general inventive concept includes a soak chamber to hold the seed, a water bath as a source of the input water, and a measuring tank where the water volume can be determined with a level sensor. The soaking temperature is maintained constant by water baths with a circulating tank surrounding the soak chamber to reduce heat loss.

19 Claims, 1 Drawing Sheet

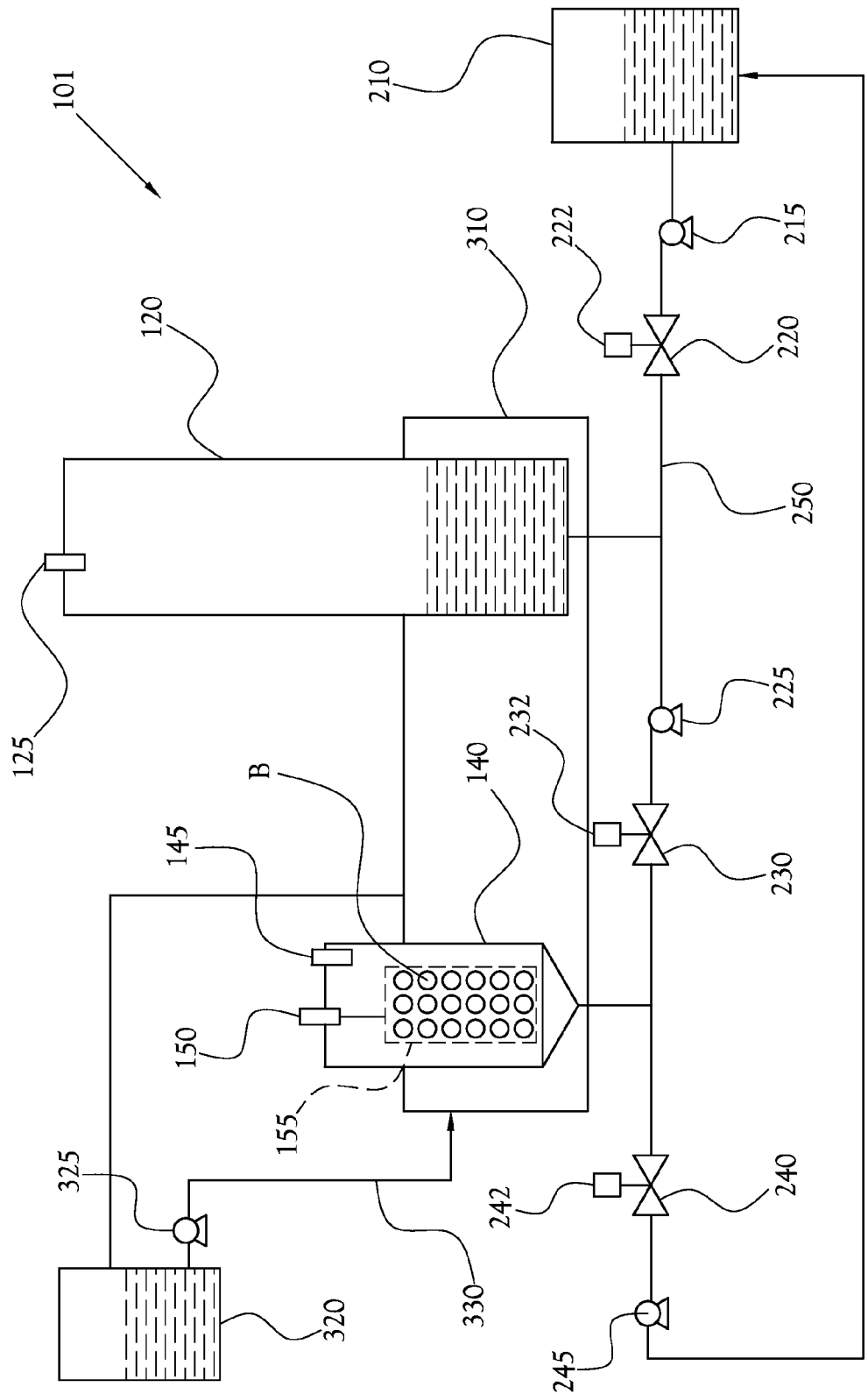

SOAK CHAMBER AND SYSTEM TO MEASURE THE SEED DENSITY HYDRATION PROFILE OF SEEDS

CROSS-REFERENCE TO RELATED APPLICATIONS

Not Applicable

STATEMENT REGARDING FEDERALLY-SPONSORED RESEARCH OR DEVELOPMENT

Not Applicable

BACKGROUND OF THE INVENTION

1. Field of Invention

The present invention relates generally to systems for preparing beans and other seeds, and in particular to apparatuses, systems and methods for measuring the seed density (weight/volume) hydration profile of seeds during soaking.

2. Description of the Related Art

The bean is a common crop but is underutilized, in part perhaps due to long soaking times required to make beans digestible. Soaking shortens the required cooking time by introducing water evenly into the dry bean seeds before cooking, thereby saving energy, reducing cost, and reducing nutrient degradation. Water distribution between protein and starch fractions also reduces time required to obtain adequate food texture. Further, soaking, under optimal conditions, facilitates the leaching of anti-nutrients that exist in legume seeds, such as tannins, phytic acids, trypsin inhibitors, and oligosaccharides that cause flatulence.

Because water absorption by bean seeds (hereinafter generally "seeds") is the first step to prepare dishes based on legumes, there is interest in developing apparatuses, systems and methods for measuring the hydration profile of seeds during soaking.

As Xu explains, dry seeds swell during hydration up to more than 250% of their original volume, with volume changes varying depending on the variety of seed. Soaking is an important unit operation during the processing of seeds used for direct consumption. The change in seed volume over time during soaking (volume kinetics) relates to water uptake and the quality of final product, and affects the design of the entire processing operation. Since volume determination is labor-intensive and time consuming, volume kinetics is usually not well monitored throughout seed hydration. Xu, Shan, "Development and application of an automatic system for determining seed volume kinetics during soaking" Master's Thesis, University of Tennessee, 2010. Xu studied volume kinetics during hydration. There is a need for apparatuses, systems and methods for measuring the full hydration profile of seeds (including volume, weight, and density) during soaking.

BRIEF SUMMARY OF THE INVENTION

Disclosed herein are apparatuses, systems and methods for measuring the hydration profile of seeds during soaking. In some embodiments, the volume change of irregular-shaped seeds during soaking is measured as the difference in the volume for a given chamber and the volume of water to fill a chamber with seeds at pre-defined time intervals. A device according to some example embodiments of the present general inventive concept includes a soak chamber to hold the seed, a water bath as a source of the input water, and a measuring tank where the water volume can be determined with a level sensor. The soaking temperature is maintained constant by water baths with a circulating tank surrounding the soak chamber to reduce heat loss.

Aspects of the present invention disclose a device and method to measure the hydration profile of seeds during soaking with accuracy. The measuring device includes a water circulator, two separate chambers, one with seed deposits and one without. A configuration of valves, pumps and sensors is arranged in a way to control the water flow from a water circulator to the chambers in series that allows for the measurement of the change in water level in the respective chambers. From the change in water level, the volume of the seeds can be determined, and from the volume and the weight, the density of the seeds can be determined.

In some embodiments of the present general inventive concept, a system for measuring the hydration profile of seeds during soaking includes a source chamber of hydration media, a measuring tank to receive hydration media from said source chamber of hydration media, said measuring tank including a sensor to measure a level of hydration media within said measuring tank, a soaking chamber to receive seeds to be tested during a hydration process and to receive hydration media from said measuring tank, said soaking chamber including a sensor, said sensor to measure a level of seeds and hydration media within said soaking chamber, and a temperature control tank to regulate the temperature within said soaking chamber.

In some embodiments, the system further includes a holder to hold seeds within said soak chamber and a load cell to weigh said seeds within said holder.

In some embodiments, said temperature control tank regulates the temperature within said soaking chamber and within said measuring tank.

In some embodiments, said temperature control tank maintains the temperature within said soaking chamber and within said measuring tank between 1° C. and 99° C.

In some embodiments, said temperature control tank maintains the temperature within said soaking chamber and within said measuring tank between 20° C. and 65° C.

In some embodiments, said temperature control tank maintains the temperature within said soaking chamber and within said measuring tank between 40° C. and 55° C.

In some embodiments, said sensor to measure a level of hydration media within said measuring tank includes an optical sensor.

In some embodiments, said sensor to measure a level of seeds and hydration media within said soaking chamber includes an optical sensor.

In some embodiments, said sensor to measure a level of seeds and hydration media within said soaking chamber includes an ultrasonic sensor.

In some embodiments of the present general inventive concept, an apparatus for measuring the hydration profile of seeds during soaking includes a source chamber of hydration media, a measuring tank to receive hydration media from said source chamber of hydration media, said measuring tank including a sensor to measure a level of hydration media within said measuring tank, a soaking chamber to receive seeds to be tested during a hydration process and to receive hydration media from said measuring tank, said soaking chamber including a sensor, said sensor to measure a level of seeds and hydration media within said soaking chamber, pumping components to convey water between said source chamber, said measuring tank, and said soaking chamber, a holder to hold seeds within said soak chamber, said holder connected to a load cell, said holder and said load cell to weigh said seeds within said holder, and a temperature control tank to regulate the temperature within said soaking chamber and said measuring tank, said temperature control tank circulating water from a water circulator, wherein the transfer of hydration media from said measuring tank to said soaking chamber facilitates a measurement of the volume of seeds within said soaking chamber during a soaking process, and wherein said load cell facilitates the weighing of the seeds within said soaking chamber during the soaking process, whereby a calculation of a density of the seeds within said soaking chamber is possible during the soaking process.

In some embodiments, said temperature control tank maintains the temperature within said soaking chamber and within said measuring tank between 1° C. and 99° C.

In some embodiments, said temperature control tank maintains the temperature within said soaking chamber and within said measuring tank between 20° C. and 65° C.

In some embodiments, said temperature control tank maintains the temperature within said soaking chamber and within said measuring tank between 40° C. and 55° C.

In some embodiments, said sensor to measure a level of hydration media within said measuring tank includes an optical sensor.

In some embodiments, said sensor to measure a level of seeds and hydration media within said soaking chamber includes an optical sensor.

In some embodiments, said sensor to measure a level of seeds and hydration media within said soaking chamber includes an ultrasonic sensor.

In some embodiments of the present general inventive concept, a method of measuring the hydration characteristics of seeds during a soaking process includes providing a device configured to make measurements of the volume and weight of seeds during a soaking process, said device including a source chamber of hydration media, a measuring tank configured to receive hydration media from said source chamber of hydration media, said measuring tank including a sensor to measure a level of hydration media within said measuring tank, a soaking chamber to receive seeds to be tested during a hydration process and to receive hydration media from said measuring tank, said soaking chamber including a sensor, said sensor to measure a level of seeds and hydration media within said soaking chamber, and a holder to hold seeds within said soak chamber, said holder connected to a load cell, said holder and said load cell to measure the weight of seeds within said holder; moving hydration media from said source chamber to said measuring tank; recording a first volume of hydration media within said measuring tank; moving hydration media from said measuring tank to said soak chamber until said soak chamber is substantially filled with hydration media; recording a second volume of hydration media within said measuring tank, whereby the difference between the first volume of hydration media within said measuring tank and the second volume of hydration media within said measuring tank indicates a volume of the soaking chamber; removing hydration media from said soaking chamber; introducing seeds into said holder within said soaking chamber; moving hydration media from said source chamber to said measuring tank; recording a third volume of hydration media within said measuring tank; moving hydration media from said measuring tank to said soak chamber until said soak chamber is substantially filled with hydration media and seeds; recording a fourth volume of hydration media within said measuring tank, whereby the difference between the third volume of hydration media within said measuring tank and the fourth volume of hydration media within said measuring tank indicates a volume of hydration media within the soaking chamber, and whereby the difference between the volume of hydration media within the soaking chamber and the volume of the soaking chamber indicates the volume of the seeds in said holder within said soaking chamber; removing hydration media from said soaking chamber; and measuring the weight of the seeds in said holder within said soaking chamber; whereby the volume of the seeds and the weight of the seeds facilitates a calculation of the density of the seeds.

In some embodiments of the method, said device configured to make measurements of the volume and weight of seeds during a soaking process includes a temperature control tank to regulate the temperature within said soaking chamber and within said measuring tank.

In some embodiments of the method, said temperature control tank maintains the temperature within said soaking chamber and within said measuring tank between 1° C. and 99° C.

In some embodiments of the method, said temperature control tank maintains the temperature within said soaking chamber and within said measuring tank between 20° C. and 65° C.

In some embodiments of the method, said temperature control tank maintains the temperature within said soaking chamber and within said measuring tank between 40° C. and 55° C.

In some embodiments of the method, said sensor to measure a level of hydration media within said measuring tank includes an optical sensor.

In some embodiments of the method, said sensor to measure a level of seeds and hydration media within said soaking chamber includes an optical sensor.

In some embodiments of the method, said sensor to measure a level of seeds and hydration media within said soaking chamber includes an ultrasonic sensor.

In some embodiments of the method, the volume of seeds and weight of seeds are measured multiple times during a soaking process.

BRIEF DESCRIPTION OF THE DRAWINGS

The above-mentioned and additional features of the invention will become more clearly understood from the following detailed description of the invention read together with the drawings in which:

FIG. 1 is a block diagram view of a system to conduct testing on seeds according to an example embodiment of the present general inventive concept.

DETAILED DESCRIPTION OF THE INVENTION

Disclosed herein are apparatuses, systems and methods for measuring the hydration profile of seeds during soaking. In some example embodiments, the volume change of irregular-shaped seeds during soaking is measured as the difference in the volume for a given chamber and the volume of water to fill a chamber with seeds at pre-defined time intervals. A device according to some example embodiments of the present general inventive concept includes a seed chamber or soak chamber (hereinafter generally "soak chamber") to hold the seed, a water bath as a source of the input water, and a measuring tank where the water volume can be determined with a level sensor. The soaking temperature is maintained constant by water baths with a circulating tank surrounding the soak chamber to reduce heat loss. A number of valves and pumps are utilized for water flow control.

Major changes to the seeds during soaking include changes in weight, volume, moisture content, and nutrient content. These changes are usually related to, and often proportional to, water uptake, and therefore an understanding of the full hydration profile of a given seed is useful for optimally designing the soak stage of food preparation. The above characteristics of the final bean food product also affect its aesthetic quality and influence the preferences of consumers.

Seed volume can increase to almost three times the original size during soaking, and the volume expansion rate of the seeds changes over time depending on the hydration characteristics of a particular seed. Because of the irregular and variable shapes of seeds, and the complex volume changes throughout the hydration process, volume determination is often a time-consuming and labor-intensive process.

Turning to the Figures, FIG. 1 illustrates a system 101 that includes one example embodiment of the present general inventive concept. The system 101 includes a measuring vessel or measuring tank 120 (often a cylindrical measuring tank) equipped with a sensor 125 (hereinafter "MT sensor") near its top to continuously measure the water level within the measuring tank. The volume of water in the measuring tank 120 is calculated by multiplying the sensor 125 level reading by the cross section area of the measuring tank 120. A soak chamber 140 to hold seeds B during the soaking process is equipped with a level sensor or "SC sensor" 145 (in some embodiments, an optical level sensor) to indicate whether water has reached the level of the SC sensor 145; generally, the soak chamber 140 also includes a mesh at the bottom to retain the seeds during the soaking process (or hydration process). A water source chamber 210 provides a source for the hydration medium (i.e., water, in most cases, although other hydration media are contemplated). The measuring tank 120, the soak chamber 140, and the water source chamber 210 are connected via flexible tubing 250 with a number of valves 220, 230, 240, pumps 215, 225, 245, and sensors 222, 232, 242 for flow control. A surrounding temperature control tank 310, within which water is continuously circulating from a second water source 320 via a circulation pump 325 and a circulation tubing line 330, is used during the soaking process in order to keep hydration temperature constant within the soak chamber 140 and the measuring chamber 120.

One example method of measuring the hydration profile of seeds during the soaking process is described herein. The first valve 220 is opened, and a first pump 215 conveys water into the measuring tank 120 until the MT sensor 125 indicates that the water level within the measuring tank 120 has reached a pre-set level (designated L0). Next, the second valve 230 is opened and a second pump 225 transfers water from the measuring tank 120 into the soak chamber 140, which was previously empty. When the SC sensor 145 indicates that the soak chamber 140 is full of water, then the second valve 230 is closed and the second pump 225 ceases to transfer water from the measuring tank 120 into the soak chamber 140. At this time the water level within the measuring tank 120 has reached a new level (designated L1), lower than L0. The interior volume of the soak chamber 140 is then substantially equal to the volume of water that has been transferred from the measuring tank 120; that is, $$V(\text{soak chamber}) = A^*(L0 - L1)$$

Next, the soak chamber 140 is drained. The third valve 240 is opened, and the third pump 245 moves water from the soak chamber 140 to the water source chamber 210.

Following the draining step, and after the third valve 240 is closed and the third pump 245 is turned off, with the soak chamber 140 substantially empty of water, seeds B are loaded into the soak chamber 140. Next, the second valve 230 is opened and the second pump 225 transfers water from the measuring tank 120 (which begins this step at level L1) into the soak chamber 140, until the SC sensor 145 indicates that the soak chamber 140 is full, at which point the second valve 230 is closed and the second pump 225 ceases to transfer water from the measuring tank 120 into the soak chamber 140. At this time, the water level within the measuring tank 120 has reached a new level (designated L2). The initial volume of the seeds (that is, V(seed-initial) or the "initial seed volume") is then calculated as $$V(\text{seed-initial}) = V(\text{soak chamber}) - A^*(L1 - L2).$$

After initial seed volume is obtained, a preset amount of time elapses for soaking the seeds B in the soak chamber 140. In many embodiments, all valves and pumps are controlled electronically via a computer, a data acquisition system and an electronic circuit board. Repeated Fill-Transfer-Drain iterations are conducted at pre-determined time intervals to obtain near real-time volume measurements during seed soaking. At any given time during the process, the volume of the seeds in the soak chamber 140 can be calculated as $$V(\text{seed}) = V(\text{soak chamber}) - V(\text{water})$$

where V(water) is the volume of water transferred from the measuring tank 120 into the soak chamber 140 during that iteration.

As noted, seed volume can increase to almost three times the original size during soaking, and the volume expansion rate of the seeds changes over time depending on the hydration characteristics of a particular seed.

In many embodiments, the soak chamber 140 is also equipped with a weight-measuring device, e.g. a load cell 150, to determine the weight of the seeds before and after each cycle of the water flow. As the seeds absorb water and other materials in the hydration medium, the weight of the seeds changes. In some embodiments, seeds B are soaked in a holder 155, as illustrated in FIG. 1, which is hanged from the load cell 150 on top of the soak chamber 140. When a holder is used for soaking, the weight of the holder, W(holder), must be into account in the calculations of seeds' weight and density. The shape of the soak chamber 140 may vary, e.g. cylindrical. It can also be cubical and rectangular or in any other shapes with a volume.

During the repeated Fill-Transfer-Drain iterations, the weight of the seeds B, both before the soaking process and during soaking process, is measured. During each iteration as described above, after the soak chamber 140 is drained, the load cell 150 records the weight of the holder 155 containing the seeds B. The weight of seeds B in the soak chamber 140 is determined as follows:

$$W(\text{seeds}) = W(\text{total}) - W(\text{holder})$$

The density of seeds, D(seeds), is determined as follows:

$$D(\text{seeds}) = W(\text{seeds}) / V(\text{seeds})$$

In some embodiments, for accuracy, before operation, the system 101 is primed to remove air bubbles from the flexible tubing 250 and other components.

In some embodiments, sensors 222, 232, 242 for are in contact or communication with the valves 220, 230, 240 in order to measure the flow of water or other hydration media. In some embodiments, the sensors 222, 232, 242, the pumps 215, 225, 245, and the valves 220, 230, 240 are all connected to or in communication with a central control system. In some embodiments, the control system includes a circuit interface board to open and close the valves and to turn the pumps on and off at appropriate times as defined by a software program.

In certain example embodiments of the present general inventive concept, as shown in the illustrated example embodiment included in FIG. 1, the temperature control tank 310, surrounds or encompasses both the soak chamber 140 and the measuring chamber 120., so as to keep hydration temperature constant within the soak chamber 140 and the measuring chamber 120 during the testing iterations. Within temperature control tank 310, water is continuously circulating from a second water source 320 via a circulation pump 325 and a circulation tubing line 330.

In various embodiments of the present general inventive concept, the water displacement principle that underlies the system allows measurement of the hydration characteristics of most irregular shaped seeds (such as lentil, rice, corn seed, barley, faba bean) during hydration without shape approximation. With high reproducible and reliable results, the system is capable of yielding data at a wide range of temperatures. Thus, apparatuses, devices, and systems according to the present general inventive concept have applicability in food industries as an effective tool for improvement of processing condition parameters and hydration behavior classification.

In several embodiments of the present general inventive concept, apparatuses, systems, devices, and methods present no difficulties in measuring volume kinetics and weight at temperatures ranging from 1° C. to 99° C., according to the temperature rating of each system or device component. Temperature is a leading factor that affects the hydration rate of foods. In many embodiments, a recommended soaking temperature for foods to have better quality and structure ranges from 20° C. to 65° C. In many embodiments, a recommended soaking temperature for foods to have better quality and structure ranges from 40° C. to 55° C.

Although in the described example embodiments detailed above, the hydration medium is water, in some embodiments, a different hydration medium is utilized. Further, in some embodiments, additives are included with water used as a hydration medium. Thus, in various embodiments, the water chemistry, e.g., pH and additives for soaking seeds, is altered. In some embodiments, the addition of salts in the hydration medium, the variance in pH of hydration medium, and other chemical properties of the medium influence the seed hydration. Systems, devices, and methods according to the present general inventive concept allow for the study of the effect of water chemistry on the hydration profiles of seeds during soaking.

In various embodiments, the hydrating medium temperature can range from 1° C. to 99° C. Sampling capacity can be range from 50 grams of dry seeds to 150 grams of dry seeds. Generally, a minimum volume measurement interval between iterations is 60 seconds, although shorter measurement intervals are contemplated. The length of the hydration process may extend over days or may encompass a much shorter time frame.

While the present invention has been illustrated by description of some embodiments, and while the illustrative embodiments have been described in detail, it is not the intention of the applicant to restrict or in any way limit the scope of the appended claims to such detail. Additional modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A system for measuring the hydration profile of seeds during soaking, comprising:
   a source chamber of hydration media;
   a measuring tank to receive hydration media from said source chamber of hydration media, said measuring tank including a sensor to measure a level of hydration media within said measuring tank;
   a soaking chamber to receive seeds to be tested during a hydration process and to receive hydration media from said measuring tank, said soaking chamber including a sensor, said sensor to measure a level of seeds and hydration media within said soaking chamber; and
   a temperature control tank to regulate the temperature within said soaking chamber and within said measuring tank.

2. The system of claim 1 further comprising a holder to hold seeds within said soak chamber and a load cell to weigh said seeds within said holder.

3. The system of claim 1 wherein said temperature control tank maintains the temperature within said soaking chamber and within said measuring tank between 1° C. and 99° C.

4. The system of claim 1 wherein said sensor to measure a level of hydration media within said measuring tank includes an optical sensor.

5. The system of claim 1 wherein said sensor to measure a level of seeds and hydration media within said soaking chamber includes an optical sensor.

6. The system of claim 1 wherein said sensor to measure a level of seeds and hydration media within said soaking chamber includes an ultrasonic sensor.

7. An apparatus for measuring the hydration profile of seeds during soaking, comprising:
   a source chamber of hydration media;
   a measuring tank to receive hydration media from said source chamber of hydration media, said measuring tank including a sensor to measure a level of hydration media within said measuring tank;
   a soaking chamber to receive seeds to be tested during a hydration process and to receive hydration media from said measuring tank, said soaking chamber including a sensor, said sensor to measure a level of seeds and hydration media within said soaking chamber;
   pumping components to convey water between said source chamber, said measuring tank, and said soaking chamber;
   a holder to hold seeds within said soak chamber, said holder connected to a load cell, said holder and said load cell to weigh said seeds within said holder; and
   a temperature control tank to regulate the temperature within said soaking chamber, said temperature control tank circulating water from a water circulator.

8. The apparatus of claim 7 wherein said temperature control tank maintains the temperature within said soaking chamber between 1° C. and 99° C.

9. The apparatus of claim 7 wherein said temperature control tank maintains the temperature within said soaking chamber between 40° C. and 55° C.

10. The apparatus of claim 7 wherein said sensor to measure a level of hydration media within said measuring tank includes an optical sensor.

11. The apparatus of claim 7 wherein said sensor to measure a level of seeds and hydration media within said soaking chamber includes an optical sensor.

12. The apparatus of claim 7 wherein said sensor to measure a level of seeds and hydration media within said soaking chamber includes an ultrasonic sensor.

13. A method of measuring the hydration characteristics of seeds during a soaking process, said method comprising:
provide a device configured to make measurements of the volume and weight of seeds during a soaking process, said device including
a source chamber of hydration media;
a measuring tank configured to receive hydration media from said source chamber of hydration media, said measuring tank including a sensor to measure a level of hydration media within said measuring tank;
a soaking chamber to receive seeds to be tested during a hydration process and to receive hydration media from said measuring tank, said soaking chamber including a sensor, said sensor to measure a level of seeds and hydration media within said soaking chamber; and
a holder to hold seeds within said soak chamber, said holder connected to a load cell, said holder and said load cell to measure the weight of seeds within said holder;
moving hydration media from said source chamber to said measuring tank;
recording a first volume of hydration media within said measuring tank;
moving hydration media from said measuring tank to said soak chamber until said soak chamber is substantially filled with hydration media;
recording a second volume of hydration media within said measuring tank, whereby the difference between the first volume of hydration media within said measuring tank and the second volume of hydration media within said measuring tank indicates a volume of the soaking chamber;
removing hydration media from said soaking chamber;
introducing seeds into said holder within said soaking chamber;
moving hydration media from said source chamber to said measuring tank;
recording a third volume of hydration media within said measuring tank;
moving hydration media from said measuring tank to said soak chamber until said soak chamber is substantially filled with hydration media and seeds;
recording a fourth volume of hydration media within said measuring tank, whereby the difference between the third volume of hydration media within said measuring tank and the fourth volume of hydration media within said measuring tank indicates a volume of hydration media within the soaking chamber, and whereby the difference between the volume of hydration media within the soaking chamber and the volume of the soaking chamber indicates the volume of the seeds in said holder within said soaking chamber;
removing hydration media from said soaking chamber; and
measuring the weight of the seeds in said holder within said soaking chamber;
whereby the volume of the seeds and the weight of the seeds facilitates a calculation of the density of the seeds.

14. The method of claim 13 wherein said device configured to make measurements of the volume and weight of seeds during a soaking process includes a temperature control tank to regulate the temperature within said soaking chamber and within said measuring tank.

15. The method of claim 14 wherein said temperature control tank maintains the temperature within said soaking chamber and within said measuring tank between 1° C. and 99° C.

16. The method of claim 13 wherein said sensor to measure a level of hydration media within said measuring tank includes an optical sensor.

17. The method of claim 13 wherein said sensor to measure a level of seeds and hydration media within said soaking chamber includes an optical sensor.

18. The method of claim 13 wherein said sensor to measure a level of seeds and hydration media within said soaking chamber includes an ultrasonic sensor.

19. The method of claim 13 wherein the volume of seeds and weight of seeds are measured multiple times during a soaking process.

* * * * *